United States Patent
Kaneko et al.

(10) Patent No.: US 8,818,479 B2
(45) Date of Patent: Aug. 26, 2014

(54) BIOLOGICAL INFORMATION DETECTION DEVICE

(71) Applicants: Takahiro Kaneko, Chiba (JP); Teruo Kato, Chiba (JP); Dai Terasawa, Chiba (JP); Hideki Okuda, Chiba (JP)

(72) Inventors: Takahiro Kaneko, Chiba (JP); Teruo Kato, Chiba (JP); Dai Terasawa, Chiba (JP); Hideki Okuda, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 13/628,131

(22) Filed: Sep. 27, 2012

(65) Prior Publication Data
US 2013/0096412 A1    Apr. 18, 2013

(30) Foreign Application Priority Data
Oct. 13, 2011  (JP) .................................. 2011-225979

(51) Int. Cl.
*A61B 5/0402*    (2006.01)
*A61B 5/0408*    (2006.01)

(52) U.S. Cl.
USPC ......................................... 600/390; 600/509

(58) Field of Classification Search
CPC ............. A61B 5/0408; A61B 5/04085; A61B 5/6831; A61B 2560/0468
USPC ................................................. 600/390, 590
See application file for complete search history.

(56) References Cited

U.S. PATENT DOCUMENTS

| | | | | |
|---|---|---|---|---|
| 3,659,586 A | * | 5/1972 | Johns et al. | 600/354 |
| 4,809,700 A | * | 3/1989 | Castelli | 600/384 |
| 5,491,474 A | * | 2/1996 | Suni et al. | 340/870.31 |
| 6,272,365 B1 | * | 8/2001 | Ronkainen et al. | 600/390 |
| 6,553,247 B1 | * | 4/2003 | Rytky | 600/386 |
| 6,600,942 B2 | * | 7/2003 | Nissila et al. | 600/372 |
| 7,167,737 B2 | * | 1/2007 | Fujii et al. | 600/390 |
| 7,526,840 B2 | | 5/2009 | Pernu et al. | 24/265 |
| D603,521 S | | 11/2009 | Lindberg et al. | D24/187 |
| 2009/0099472 A1 | * | 4/2009 | Remmert et al. | 600/534 |
| 2009/0234201 A1 | | 9/2009 | Huang et al. | 600/301 |
| 2010/0191090 A1 | * | 7/2010 | Shin et al. | 600/388 |

FOREIGN PATENT DOCUMENTS

WO    2011039663    4/2011

* cited by examiner

*Primary Examiner* — Lee S Cohen
(74) *Attorney, Agent, or Firm* — Adams & Wilks

(57) ABSTRACT

A biological information detection device has a main body portion, a biological signal detection portion formed integrally with the main body portion, a mounting portion for detachably mounting the main body portion and the biological signal detection portion to a human body, and an engagement portion for detachably mounting the main body portion to the mounting portion. The biological signal detection portion has electrodes configured to be brought into contact with a biological surface of the human body. The engagement portion includes first connecting members protruding from respective opposite sides of the main body portions at positions corresponding to the electrodes, and second connecting members extending from respective end portions of the mounting portion for detachable engagement with the respective first connecting members.

12 Claims, 8 Drawing Sheets

BIOLOGICAL INFORMATION DETECTION DEVICE

BACKGROUND OF THE INVENTION

1. Field of the Invention

The present invention relates to a biological information detection device that detects a biological signal by installing an electrode on the biological surface of the human body.

2. Background Art

Among these kinds of biological information detection devices, there is, for example, a device that detects an electro-cardiac signal generated in association with a heartbeat, and measures a heart rate from the biological surface. As such a biological information detection device, there is, for example, a device which includes a main body portion having a detection circuit board and the like built-in, and a strap for mounting the main body portion to the human body, the strap being provided with a pair of electrodes. The main body portion and the strap are provided with an electrical connection portion for electrically connecting a detection circuit board of the main body portion to an electrode of the strap.

Based on such a configuration, an electro-cardiac signal generated in association with a heartbeat is detected by bringing a pair of electrodes into contact with the chest (biological surface) of the human body, and the main body portion derives a heart rate on the basis of the detected electro-cardiac signal.

Further, among the biological information detection devices, there is, for example, a device in which the main body portion is detachably provided to the strap from the viewpoint of maintenance, such as cleaning of the strap. When the main body portion is mounted to the strap, the electrical connection portion provided to the strap and the electrical connection portion provided to the main body portion are mechanically connected to each other, and the detection circuit board and the electrode are electrically connected to each other (see, for example, Specification of U.S. Pat. No. 7,526,840).

SUMMARY OF THE INVENTION

However, in the above-mentioned related art, since the main body portion and the electrode are formed to be detachable from each other, there is a problem that the detection performance of the heartbeat measurement device becomes unstable depending on the installation conditions of the electrical connection portion. In addition, there is concern of the electrical connection portion being damaged by repeatedly performing attaching and detaching operations of the main body portion and the electrode.

Further, since the strap is provided with an electrode, external force in the tensile direction is applied to the electrode and the electrical connection portion at all times, in a state where the heartbeat measurement device is installed on the human body. For this reason, there is a concern that the electrical connection portion provided to the strap and the electrical connection portion provided to the main body portion are mechanically separated from each other, and thus that the electrical connection between the detection circuit board and the electrode are cut off. In addition to this, there is also the concern that the electrode portion is exposed to a cleaning solution in association with cleaning of the strap at the time of maintenance, and thus that electrical parts such as the electrode and the electrical connection portion are damaged.

Consequently, the present invention is contrived in view of such circumstances, and an object thereof is to provide a biological information detection device capable of preventing defects from occurring in electrical parts such as the electrode and the electrical connection portion while securing good maintenance, and preventing the detection performance from becoming unstable.

According to an aspect of the present invention, there is provided a biological information detection device including: a device main body; a biological signal detection portion, formed integrally with the device main body, which has an electrode that comes into contact with a biological surface; and a fixing portion, formed in a belt shape, which fixes the device main body and the biological signal detection portion to a human body, wherein both ends of the fixing portion in a long-side direction are detachably installed on the device main body through an engagement portion.

According to the foregoing aspect of the present invention, since the device main body and the biological signal detection portion can be fixed to the human body in a state where the fixing portion and the biological signal detection portion including the electrode are separated from each other, it is possible to prevent external force from being applied to the biological signal detection portion. In addition, the device main body and the biological signal detection portion can be separated from the fixing portion in a state where the device main body and the biological signal detection portion are formed integrally with each other. For this reason, it is possible to perform cleaning of a simple fixing portion while securing good maintenance, and to reliably prevent defects from occurring in electrical parts such as the electrode and the electrical connection portion.

Further, since both ends of the fixing portion in the long-side direction are connected to the device main body, it is possible to accurately perform positioning of the device main body with respect to the fixing portion, and to prevent displacement thereof. For this reason, it is possible to provide the biological information detection device having good installation stability.

In addition, the fixing portion may include at least an elastic strap, and a non-elastic belt connected to at least one of one end and the other end of the strap in a long-side direction. The belt may be formed so as to cover the biological signal detection portion, and may be detachably installed on the device main body through the engagement portion.

According to the foregoing aspect of the present invention, the biological signal detection portion is prevented from being exposed by covering the biological signal detection portion using the belt, and thus it is possible to prevent the electrode of the biological signal detection portion from being short-circuited through clothes or the like, and to improve designability. In addition, since the belt is non-elastic, it is possible to more accurately perform positioning of the device main body with respect to the fixing portion.

In addition, a displacement regulation portion that regulates displacement of a relative position may be provided between the belt and the biological signal detection portion.

According to the foregoing aspect of the present invention, the electrode is able to be caused to reliably adhere tightly to the chest of the user, and thus it is possible to improve detection accuracy of the biological information detection device. In addition, displacement between the belt and the biological signal detection portion is able to be prevented from occurring, and thus it is possible to reliably prevent the electrode of the biological signal detection portion from being short-circuited through clothes or the like due to exposure of the biological signal detection portion from the belt.

In addition, the engagement portion may be constituted by a hook portion provided to one of the device main body and the fixing portion, and an engaged portion, provided to the other one of the device main body and the fixing portion, which is engaged with the hook portion.

According to the foregoing aspect of the present invention, it is possible to reliably prevent the device main body from falling off the fixing portion at the time of mounting the biological information detection device, and to easily perform attachment and detachment of the device main body and the fixing portion to and from each other at the time of maintenance.

In addition, the biological signal detection portion may be formed from a conductive elastomer, and the conductive elastomer serves as the electrode.

According to the foregoing aspect of the present invention, it is possible to easily elastically deform the biological signal detection portion, and to increase adhesion of the electrode to the biological surface. For this reason, it is possible to detect the biological signal with a higher degree of accuracy.

According to the present invention, since the device main body and the biological signal detection portion can be fixed to the human body in a state where the fixing portion and the biological signal detection portion including the electrode are separated from each other, it is possible to prevent external force from being applied to the biological signal detection portion. In addition, the device main body and the biological signal detection portion can be separated from the fixing portion in a state where the device main body and the biological signal detection portion are formed integrally with each other. For this reason, it is possible to perform cleaning of the simple fixing portion while securing good maintenance, and to reliably prevent defects from occurring in electrical parts such as the electrode and the electrical connection portion.

Further, since both ends of the fixing portion in the long-side direction are connected to the device main body, it is possible to accurately perform positioning of the device main body with respect to the fixing portion, and to prevent displacement thereof. For this reason, it is possible to provide the biological information detection device having good installation stability.

DETAILED DESCRIPTION OF THE INVENTION

First Embodiment (Heartbeat Measurement Device)

Next, a first embodiment of the present invention will be described with reference to the drawings.

Figure 1:
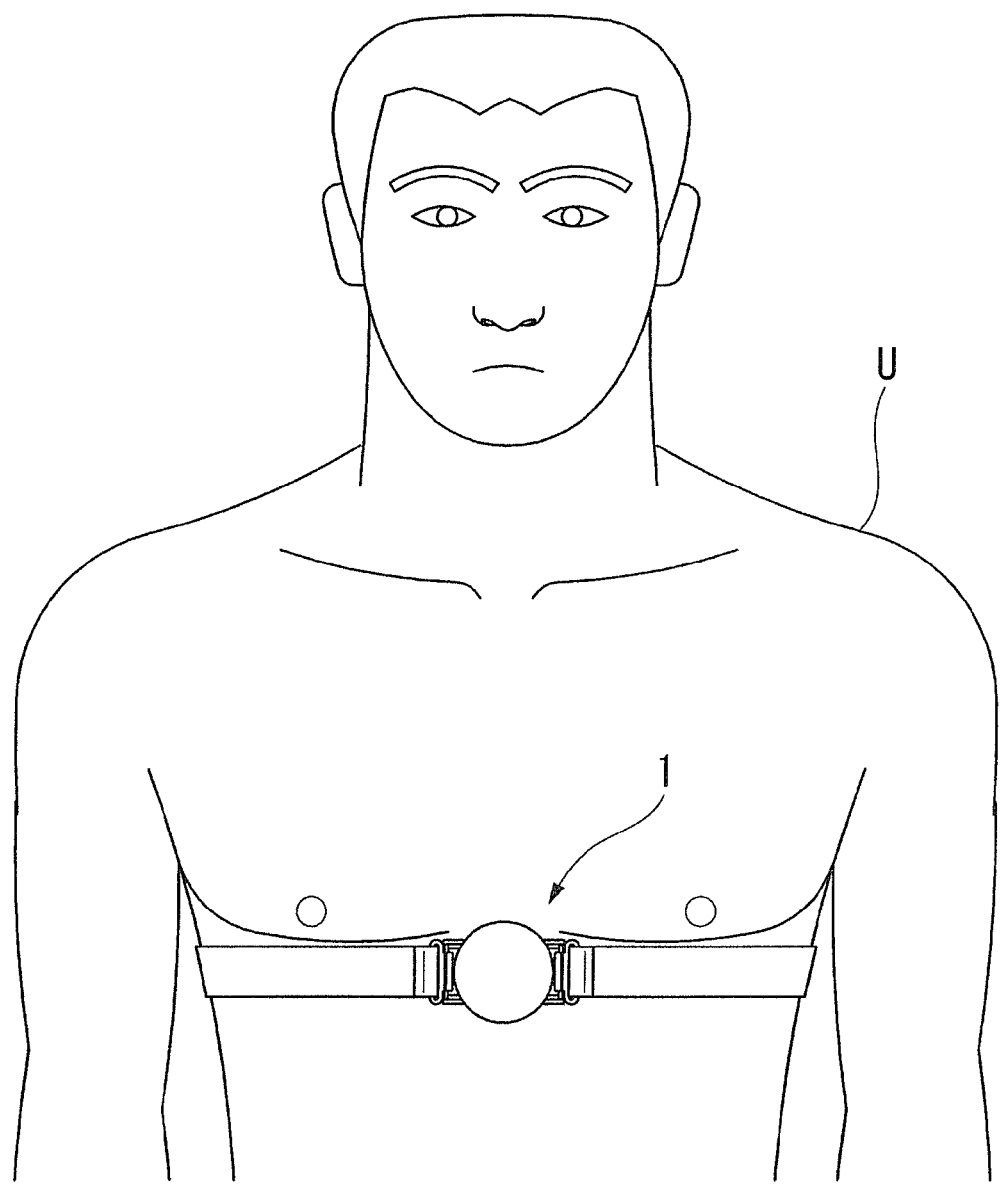
FIG. 1 is an explanatory diagram illustrating a state where a heartbeat measurement device according to a first embodiment of the present invention is installed on a user.
Figure 2:
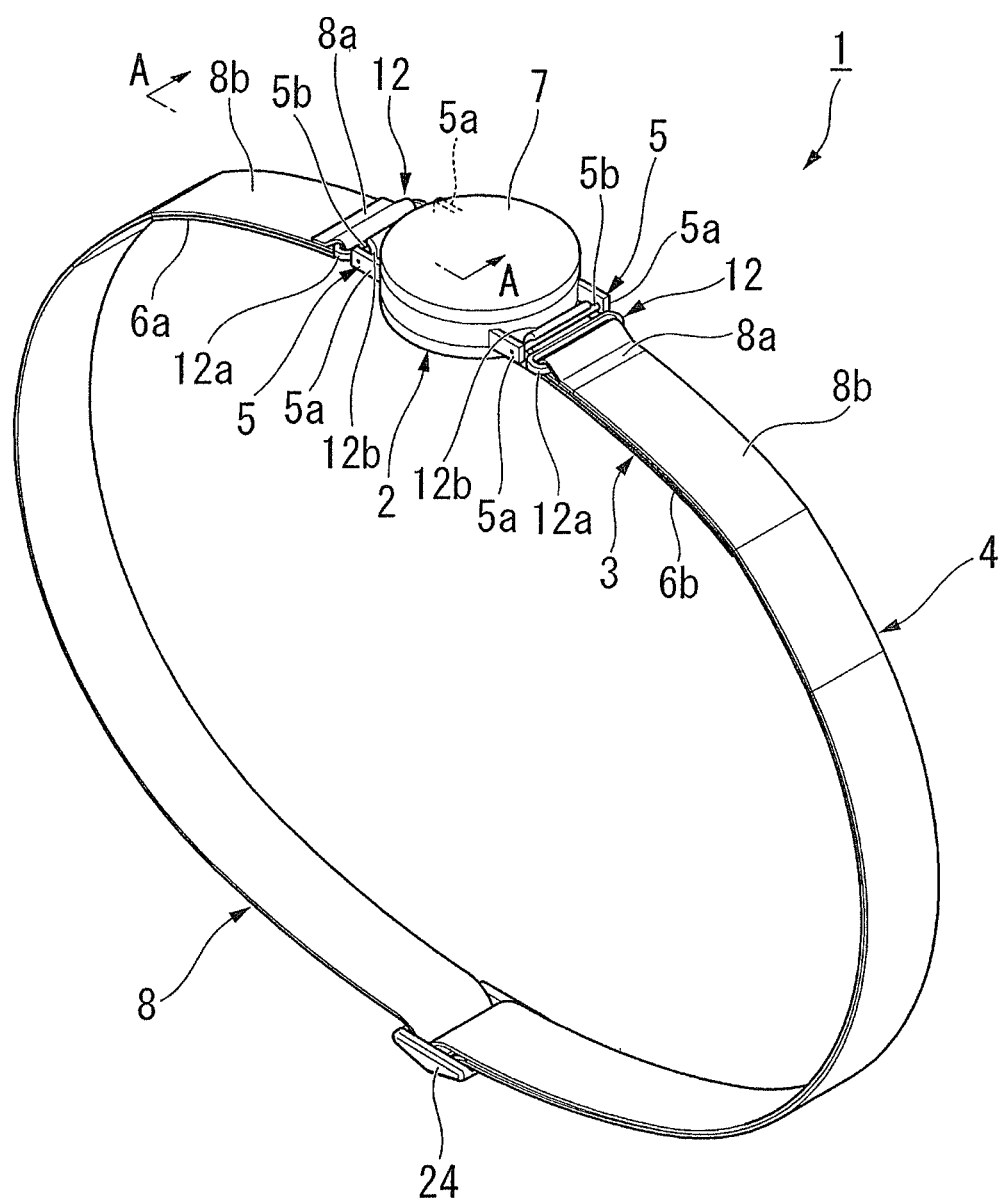
FIG. 2 is a perspective view illustrating the heartbeat measurement device according to the first embodiment.
Figure 3:
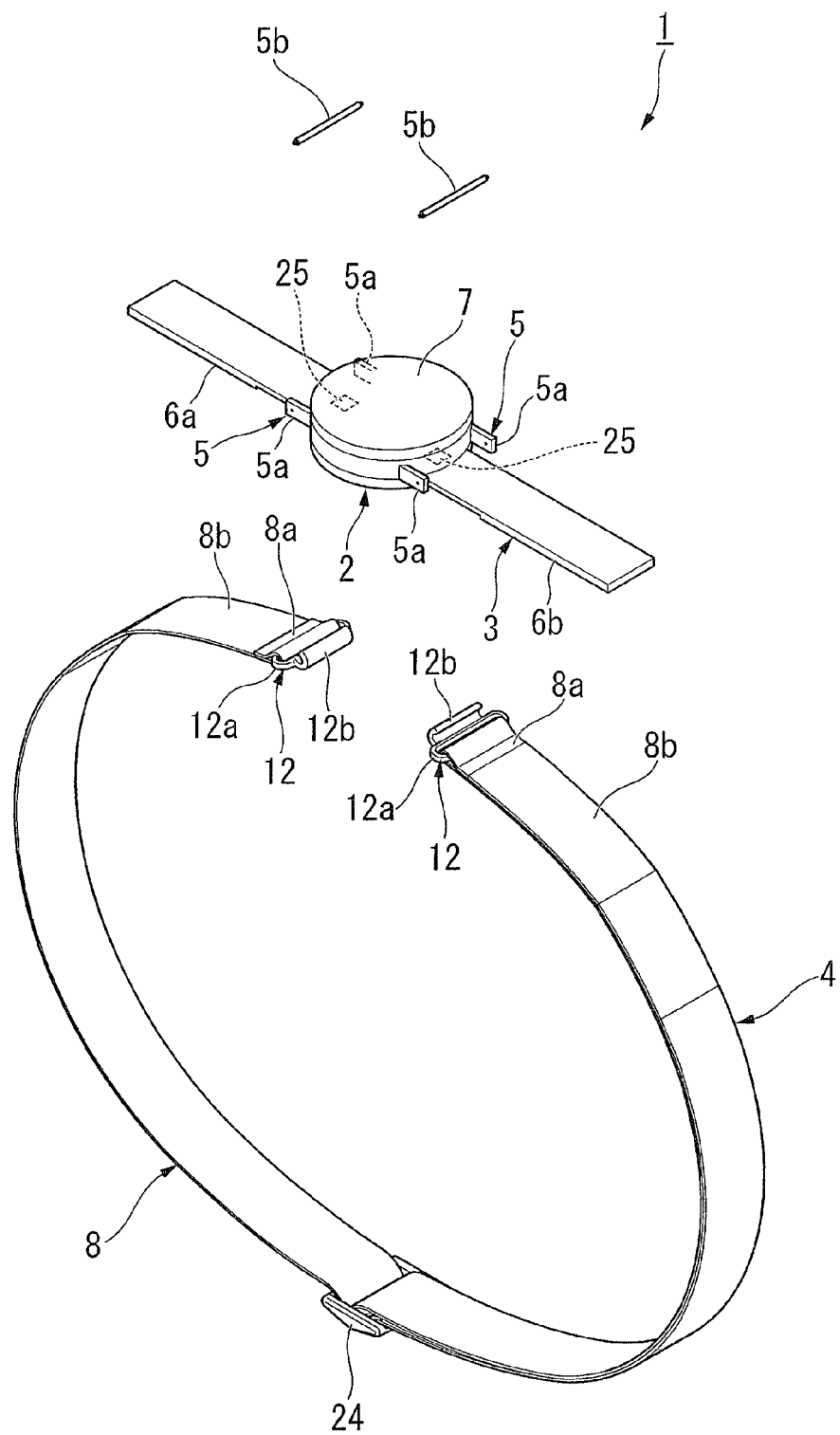
FIG. 3 is an exploded perspective view illustrating the heartbeat measurement device according to the first embodiment.

FIG. 1 is an explanatory diagram illustrating a state where a heartbeat measurement device 1 which is a biological information detection device according to the present invention is installed on a user U, FIG. 2 is a perspective view illustrating the heartbeat measurement device 1, and FIG. 3 is an exploded perspective view illustrating the heartbeat measurement device 1.

As shown in FIG. 1, the heartbeat measurement device 1 is mounted to the chest which is a biological surface of the user U to detect an electro-cardiac signal generated in association with heartbeat, and wirelessly communicates the detected electro-cardiac signal. As shown in FIG. 2, the heartbeat measurement device 1 includes a device main body 2, a heartbeat detection portion 3 formed integrally with the device main body 2, and a fixing band (mounting portion) 4 for mounting the device main body 2 and the heartbeat detection portion 3 to the chest of the user U (see FIG. 1).

The device main body 2 includes a case 7 of which the external shape is formed in a substantially disk shape, and a detection circuit board (not shown) provided within the case 7. Meanwhile, the external shape of the case 7 is not limited to the substantial disk shape of the embodiment, but may be, for example, rectangular plate-shaped.

A detection circuit board (not shown) includes a wireless transmission portion and a transmitter circuit (both not shown), and performs wireless communication on the basis of the signal detected by the heartbeat detection portion 3. The heartbeat detection portion 3 is electrically connected to the detection circuit board.

As shown in FIG. 3, the heartbeat detection portion 3 is constituted by a pair of electrodes 6a and 6b. The electrodes 6a and 6b are made of a belt-like conductive elastomer, and one-side ends thereof in the long-side direction are connected to both sides with the device main body 2 interposed therebetween. The electrodes 6a and 6b are electrically connected to the detection circuit board through an electrical connection portion 25 provided to the electrodes 6a and 6b and the detection circuit board (not shown) of the device main body 2.

Meanwhile, as the conductive elastomer, for example, conductive silicon rubber mixed with carbon black, conductive rubber mixed with carbon black, conductive polyurethane rubber mixed with carbon black, or the like can be used.

In the case 7, a pair of connection members 5 (first connecting members) are provided at positions corresponding to the pair of electrodes 6a and 6b. Each connection member 5 is constituted by a pair of arms 5a extended out from the outer circumferential surface of the case 7 toward the radial outside of the case 7 along the belt-like electrodes 6a and 6b, and a rod-shaped engaged portion 5b extending so as to be laid across a pair of arms 5a. The engaged portion 5b of the connection member 5 is formed detachably to a hook portion 12b of a strap attaching and detaching member (second connecting member) 12 provided to an elastic strap 8 described later.

(Fixing Band)

The fixing band 4 is formed in a substantially ring shape so as to be mounted over the whole circumference of the chest of the user U (see FIG. 1). Specifically, the fixing band 4 is the elastic strap 8 having elasticity which is formed in a belt shape, and the device main body 2 is connected thereto so as to be laid across both ends of the elastic strap 8 in the long-side direction.

A length adjustment member 24 for adjusting the length of the elastic strap 8 is provided substantially at the center of the elastic strap 8 in the long-side direction.

The strap attaching and detaching member 12 capable of attaching and detaching the elastic strap 8 and the device main body 2 is provided on both ends of the elastic strap 8 in the long-side direction. The strap attaching and detaching member 12 is constituted by an elliptically ring-shaped frame body 12a and the hook portion 12b curvedly formed from a region located along the long-side direction of the frame body 12a toward the radial outside of the frame body 12a. Meanwhile, the frame body 12a and the hook portion 12b may be formed integrally with each other, or may be bonded to each other after they are formed separately.

Figure 4:
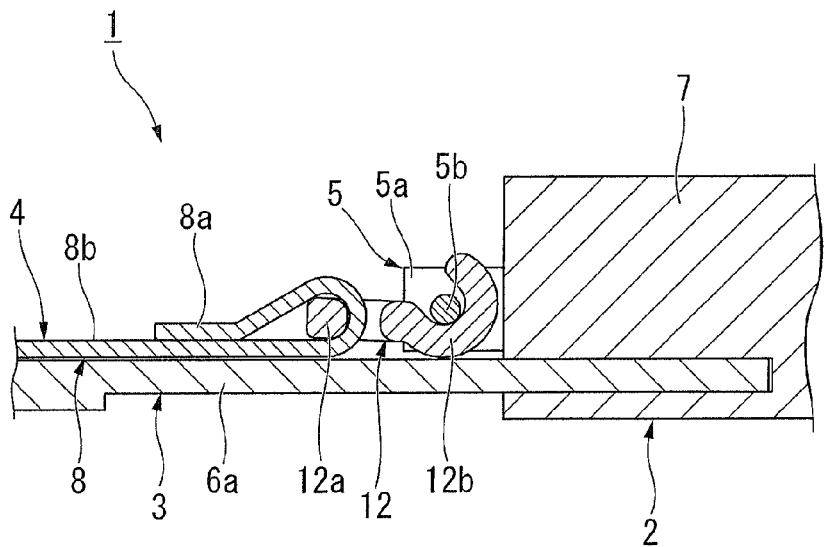
FIG. 4 is a cross-sectional view taken along the line A-A of FIG. 2.

FIG. 4 is a cross-sectional view taken along the line A-A of FIG. 2.

As shown in FIG. 4, in the strap attaching and detaching member 12 and the elastic strap 8, after an elastic strap end 8a is inserted into the frame body 12a, the strap end is folded back to the side opposite to the hook portion 12b, and an elastic strap body 8b and the elastic strap end 8a are fixed and installed. The elastic strap body 8b and the elastic strap end 8a are fixed to each other by sewing, a hook-and-loop fastener or the like.

The elastic strap 8 and the device main body 2 are detachably installed by engaging the hook portion 12b of the strap attaching and detaching member 12 with the engaged portion 5b of the connection member 5. That is, the hook portion 12b of the strap attaching and detaching member 12 and the engaged portion 5b of the connection member 5 constitute an engagement portion of the elastic strap 8 and the device main body 2. Thereby, it is possible to reliably prevent the device main body 2 from falling off the fixing band 4 at the time of mounting the heartbeat measurement device, and to easily perform attachment and detachment of the device main body 2 and the fixing band 4 to and from each other at time of maintenance.

Herein, when the hook portion 12b of the strap attaching and detaching member 12 is engaged with the engaged portion 5b of the connection member 5, it is preferable that an opening of the hook portion 12b is disposed on the opposite side to the electrode 6a. Thereby, the electrode 6a is prevented from being damaged due to the tip of the hook portion 12b, and the hook portion 12b is prevented from falling off when the heartbeat detection portion 3 is mounted.

The heartbeat measurement device 1 is mounted to the chest of the user U (see FIG. 1) in accordance with the following procedure based on the foregoing described configuration.

As shown in FIG. 2, the hook portion 12b of one (for example, right side in FIG. 2) strap attaching and detaching member 12 out of the strap attaching and detaching member 12 provided on both ends of the fixing band 4, and the engaged portion 5b of one connection member 5 out of a pair of connection members 5 provided to the device main body 2 are engaged with each other.

Subsequently, while the device main body 2 is disposed at the center of the chest of the user U in a state where one hook portion 12b and one engaged portion 5b are engaged with each other, the electrodes 6a and 6b are brought into contact with the surface of the human body of the user U and the fixing band 4 is wound around the chest of the user U. The hook portion 12b of the other (for example, left side in FIG. 2) strap attaching and detaching member 12 and the engaged portion 5b of the other connection member 5 are engaged with each other. Thereby, the fixing band 4 is installed on the chest of the user U.

Finally, the length of the elastic strap 8 of the fixing band 4 is adjusted by the length adjustment member 24. Since the elastic strap 8 has elasticity, the length of the entire fixing band 4 is set to be slightly shorter than the chest circumference of the user U, so that the elastic strap 8 is elongated slightly, and adhesion of the fixing band 4 and the electrodes 6a and 6b to the user U increases.

As stated above, the mounting of the heartbeat measurement device 1 to the user U is completed. That is, in a state where the fixing band 4 and the heartbeat detection portion 3 are separated from each other, the heartbeat detection portion 3 and the device main body 2 are fixed to the user U. An electro-cardiac signal generated in association with a heartbeat is detected by the pair of electrodes 6a and 6b. The detection circuit board (not shown) of the device main body 2 wirelessly communicates the electro-cardiac signal detected by the pair of electrodes 6a and 6b.

(Effect)

According to the first embodiment, in a state where the fixing band 4 and the heartbeat detection portion 3 having the electrodes 6a and 6b are separated from each other, the device main body 2 and the heartbeat detection portion 3 can be fixed to the user U, and thus it is possible to prevent an external force from being applied to the heartbeat detection portion 3 having the electrodes 6a and 6b. In addition, since the device main body 2 and the heartbeat detection portion 3 can be separated from the fixing band 4 in a state where the device main body 2 and the heartbeat detection portion 3 are formed integrally with each other, it is possible to easily perform cleaning of only the fixing band 4. At this time, as in conventional cases, since the fixing band 4 is not provided with the electrodes 6a and 6b, it is possible to reliably prevent defects from occurring in electrical parts such as the electrodes 6a and 6b and the electrical connection portion 25. In this manner, in the heartbeat measurement device 1, it is possible to perform cleaning of the simple fixing band 4 while securing good maintenance, and can reliably prevent defects from occurring in electrical parts such as the electrodes 6a and 6b and the electrical connection portion 25.

Further, since both ends of the fixing band 4 in the long-side direction are connected to the device main body 2, it is possible to accurately perform positioning of the device main body 2 with respect to the fixing band 4, and to prevent displacement thereof. For this reason, it is possible to provide the heartbeat measurement device 1 having good installation stability.

In addition, the fixing band 4 and the device main body are detachably installed by the engagement portion constituted by the hook portion 12b of the strap attaching and detaching member 12 provided to the fixing band 4 and the engaged portion 5b of the connection member 5 provided to the device main body 2. Therefore, it is possible to reliably prevent the device main body 2 from falling off the fixing band 4 at the time of mounting the heartbeat measurement device 1, and to easily perform attachment and detachment of the device main body 2 and the fixing band 4 to and from each other at the time of maintenance.

In addition, the electrodes 6a and 6b are formed from a conductive elastomer and thus are soft, and are pressed to the fixing band 4. Thereby, the electrodes are elastically deformed along the chest of the user U. For this reason, the electrodes 6a and 6b reliably adhere tightly to the chest of the user U. Therefore, it is possible to detect an electro-cardiac signal with a higher degree of accuracy.

Second Embodiment

Figure 5:
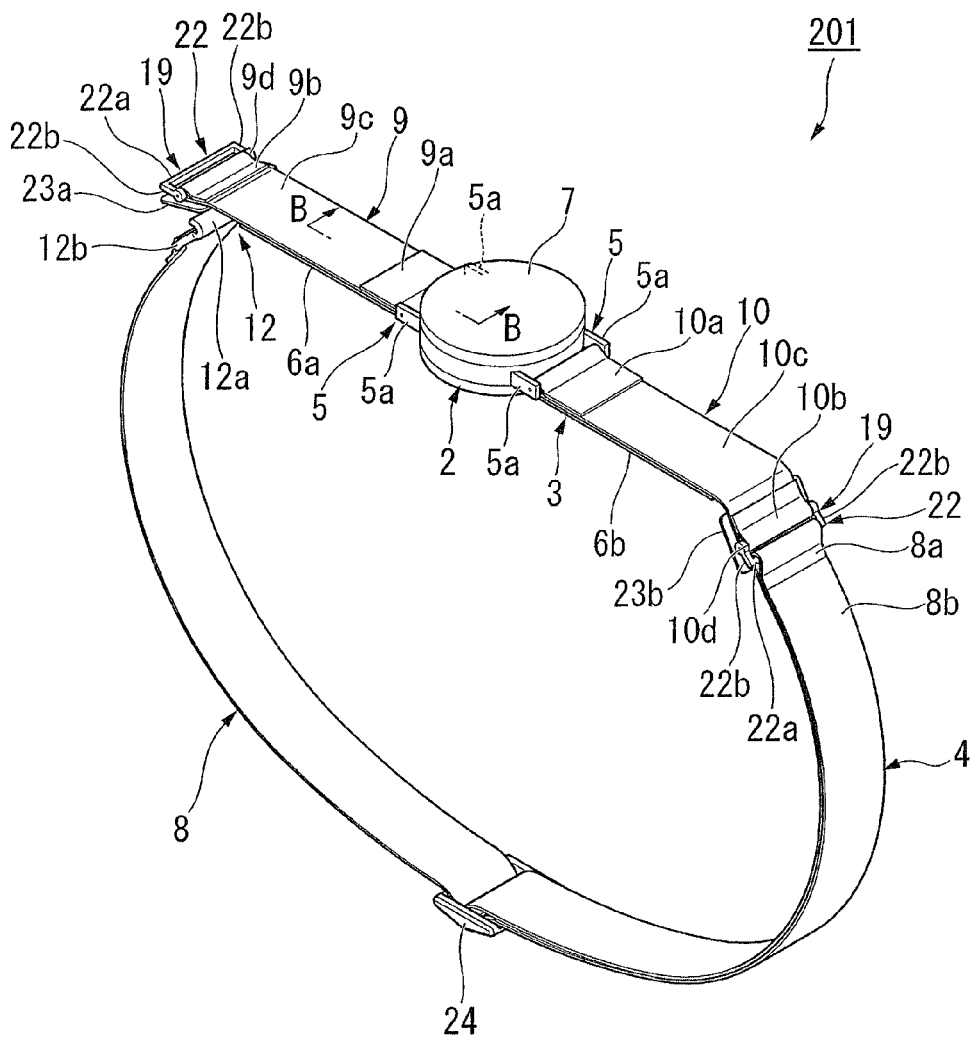
FIG. 5 is a perspective view illustrating a heartbeat measurement device according to a second embodiment.
Figure 6:
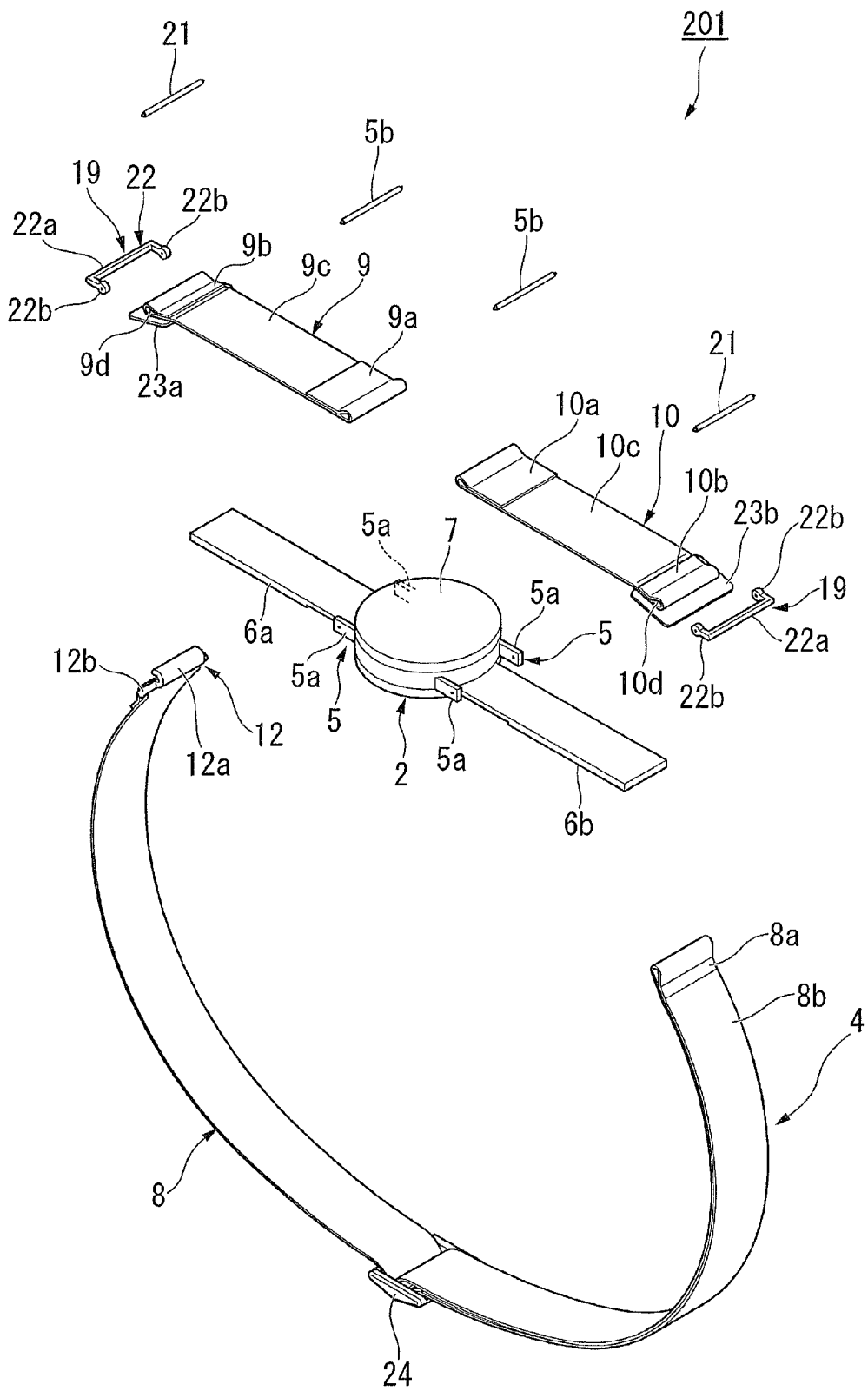
FIG. 6 is an exploded perspective view illustrating the heartbeat measurement device according to the second embodiment.

FIG. 5 is a perspective view illustrating a heartbeat measurement device 201 according to a second embodiment, and FIG. 6 is an exploded perspective view illustrating the heartbeat measurement device 201 according to the second embodiment.

Subsequently, the heartbeat measurement device 201 according to the second embodiment will be described with reference to FIGS. 5 and 6.

The heartbeat measurement device 1 according to the first embodiment is configured such that the fixing band 4 is formed by the elastic strap 8, and the elastic strap 8 and the device main body 2 are formed detachably.

On the other hand, the heartbeat measurement device 201 according to the second embodiment is different from the heartbeat measurement device 1 according to the first embodiment, in that the fixing band 4 is formed by the elastic strap 8 and belts 9 and 10, and the belts 9 and 10 and the device main body 2 are formed detachably.

Meanwhile, detailed description of the same configurations as those of the first embodiment such as the configuration in which the heartbeat detection portion 3 and the fixing band 4 are separated from each other will be omitted.

As shown in FIG. 5, the fixing band 4 includes the elastic strap 8, formed in a belt shape, which has elasticity and a pair of non-elastic belts 9 and 10, formed in a belt shape, which are connected to both ends of the elastic strap 8 in the long-side direction.

A pair of belts 9 and 10 are formed in a substantially belt shape by a fiber material, and are disposed so as to cover the electrodes 6a and 6b of the heartbeat detection portion 3 from the outside at both sides with the device main body 2 interposed therebetween. Meanwhile, the belt 9 disposed at the electrode 6a side and the belt 10 disposed at the electrode 6b side are the same as each other in shape. Therefore, hereinafter, description of the belt 9 disposed at the electrode 6a side will be made, while description of the belt 10 disposed at the electrode 6b side will be omitted.

As shown in FIG. 6, a ring portion 9d formed by folding back an end 9b of the belt 9 is provided at the elastic strap 8 side in the long-side direction of the belt 9. The ring portion 9d is provided with a strap connector 19 capable of being connected to the elastic strap 8. The strap connector 19 is constituted by a shaft 21 inserted into the ring portion 9d and a connector body 22 provided so as to be laid across both ends of the shaft 21.

The tip of the shaft 21 is configured to freely come in and out, and to be in a state where it is biased toward the tip side by a spring (not shown).

The connector body 22 is formed in an approximately lateral U-shape when seen in a plan view, and is a component in which a shaft portion 22a and a pair of arm portions 22b and 22b curvedly extended from both ends of the shaft portion 22a toward the shaft 21 are formed integrally with each other.

The strap connector 19 is formed in a rectangular frame shape by disposing the shaft 21 between a pair of arm portions 22b and 22b, and is installed at the elastic strap 8 side in the long-side direction of the belt 9.

Figure 7:
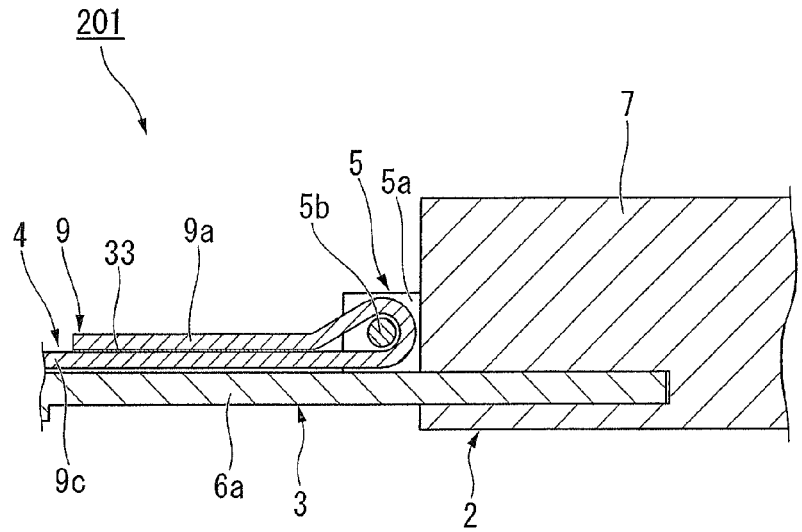
FIG. 7 is a cross-sectional view taken along the line B-B of FIG. 5.

FIG. 7 is a cross-sectional view taken along the line B-B of FIG. 5.

As shown in FIG. 7, at the device main body 2 side in the long-side direction of the belt 9, after a belt end 9a is inserted between the device main body 2 and the engaged portion 5b of the connection member 5, the belt end is folded back to the side opposite to the device main body 2, and a belt body 9c and the belt end 9a are fixed and installed onto the device main body 2.

Herein, between the belt body 9c and the belt end 9a, a hook-and-loop fastener 33 is provided to the belt body 9c and the belt end 9a. Thereby, the belt body 9c and the belt end 9a are detachably installed, and the belt 9 and the device main body 2 are detachably installed. That is, the hook-and-loop fastener 33 provided to the belt body 9c and the belt end 9a constitutes an engagement portion between the belt 9 and the device main body 2. Thereby, it is possible to reliably prevent the device main body 2 from falling off the belt 9 at the time of mounting the heartbeat measurement device 201, and to easily perform attachment and detachment of the device main body 2 and the belt 9 to and from each other at the time of maintenance.

As shown in FIG. 5, a pair of belts 9 and 10 are respectively connected to both ends of the elastic strap 8. The strap attaching and detaching member 12 is provided at the electrode 6a side of the elastic strap 8, and the hook portion 12b of the strap attaching and detaching member 12 and the shaft portion 22a of the strap connector 19 are engageable with each other. Thereby, the electrode 6a side of the elastic strap 8 and the belt 9 are detachably installed.

In addition, at the electrode 6b side of the elastic strap 8, after the elastic strap end 8a is inserted into the strap connector 19, the strap end is folded back to the side opposite to the belt 9 and the elastic strap end 8a is fixed to the elastic strap body 8b. Thereby, the electrode 6b side of the elastic strap 8 and the belt 9 are connected to each other.

Meanwhile, belt-like human body protective portions 23a and 23b for preventing the strap attaching and detaching member 12 and the strap connector 19 from being exposed to the inner surface side, that is, preventing from being exposed to the side of the chest of the user U (see FIG. 1) are installed on the ring portions 9d and 10d of the belts 9 and 10. Thereby, there is no case where the strap attaching and detaching member 12 and the strap connector 19 come into direct contact with the chest of the user U, and thus the user U feels no sense of discomfort.

(Effect of Second Embodiment)

According to the second embodiment, in the heartbeat measurement device 1, since it is possible to perform cleaning of the simple fixing band 4 while securing good maintenance similarly to the first embodiment, it is possible to reliably prevent defects from occurring electrical parts such as the electrodes 6a and 6b and the electrical connection portion 25. Further, the heartbeat detection portion 3 is prevented from being exposed by covering the heartbeat detection portion 3 using the belts 9 and 10, and thus it is possible to prevent the electrodes 6a and 6b of the heartbeat detection portion 3 from being short-circuited to each other through clothes or the like, and to improve designability. In addition, since the belts 9 and 10 are non-elastic, it is possible to more accurately perform positioning of the device main body 2 with respect to the fixing band 4.

(First Modified Example of Second Embodiment)

Figure 8:
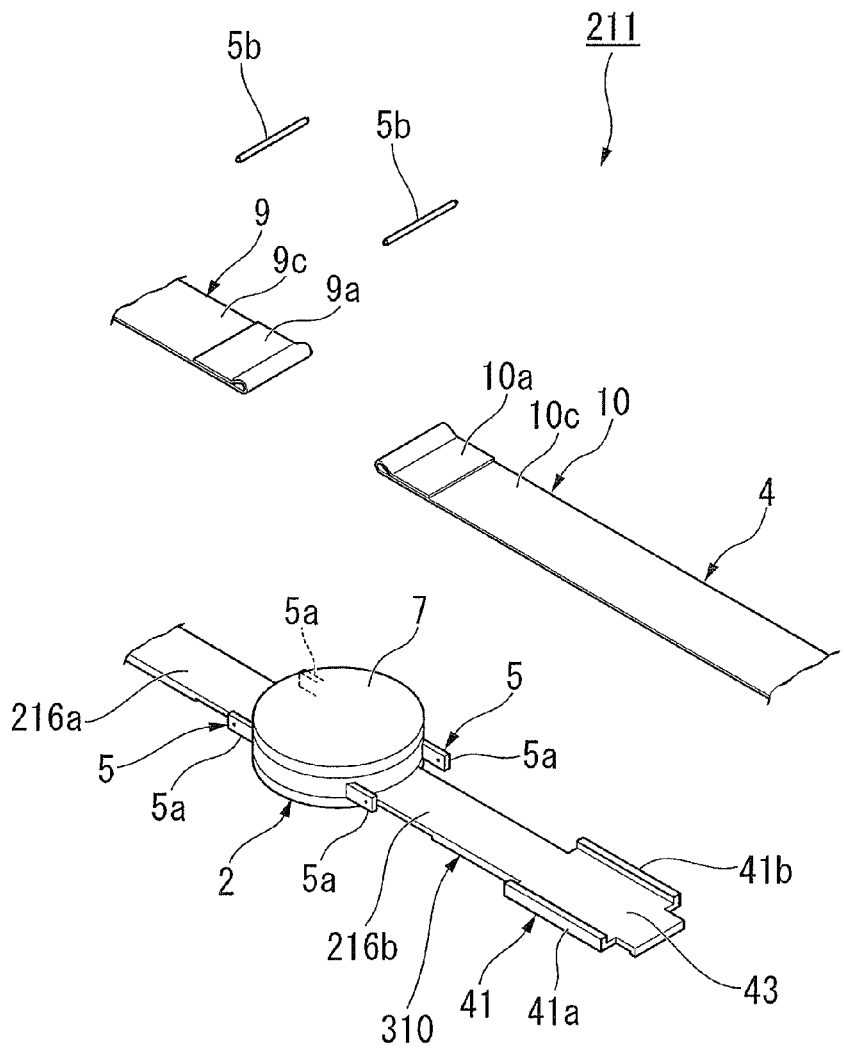
FIG. 8 is a perspective view illustrating the periphery of an electrode according to a first modified example of the second embodiment.

FIG. 8 is a perspective view illustrating the periphery of electrodes 216a and 216b according to a first modified example of the second embodiment.

Figure 9:
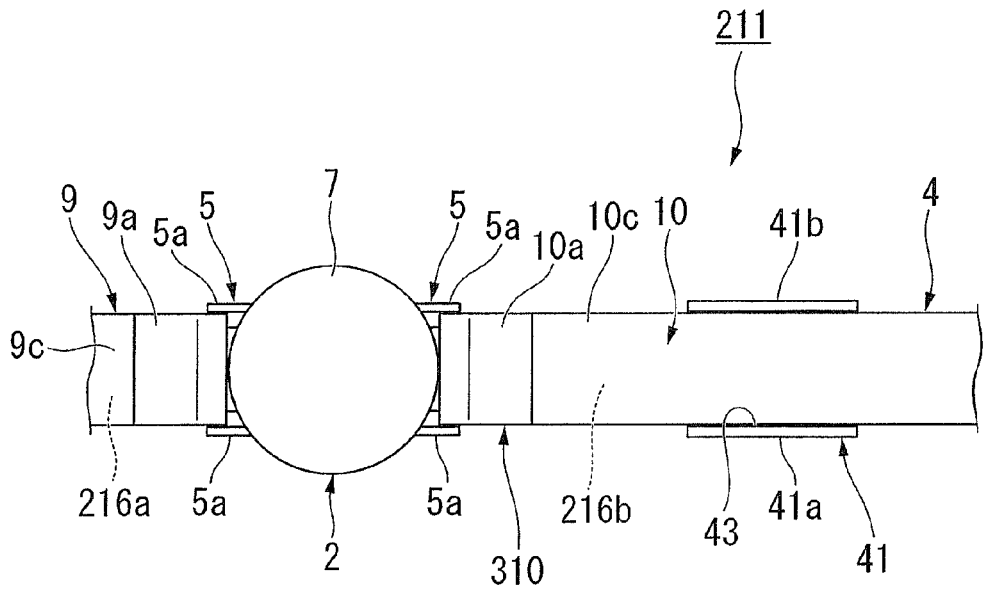
FIG. 9 is a top view illustrating the periphery of the electrode according to the first modified example of the second embodiment.

FIG. 9 is a top view illustrating the periphery of the electrodes 216a and 216b according to the first modified example of the second embodiment.

Subsequently, a heartbeat measurement device 211 according to the first modified example of the second embodiment will be described with reference to FIGS. 8 and 9.

In the heartbeat measurement device 201 according to the second embodiment, a pair of belts 9 and 10 are disposed so as to cover the electrodes 6a and 6b of the heartbeat detection portion 3 from the outside. On the other hand, the heartbeat measurement device 211 according to the first modified example of the second embodiment is different from that in the above-mentioned embodiment, in that the pair of belts 9 and 10 are disposed so as to cover the electrodes 216a and 216b of the heartbeat detection portion 310 from the outside, and a guide portion 41 is further formed in the electrodes 216a and 216b. Meanwhile, detailed description of the same configuration as that of the second embodiment will be omitted.

In addition, in FIGS. 8 and 9, the guide portion 41 on the belt 10 side is shown and the guide portion 41 on the belt 9 side is not shown, but the guide portion 41 on the belt 10 side and the guide portion 41 on the belt 9 side have the same structure as each other. Hereinafter, description of the guide portion 41 on the belt 10 side will be made, while description of the guide portion 41 on the belt 9 side will be omitted.

(Guide Portion)

In the electrode 216b, the guide portion 41 is formed on the end on the opposite side (right side in FIGS. 8 and 9) to the device main body 2. The guide portion 41 is constituted by two walls 41a and 41b formed upright from both sides of the electrode 216b in the short-side direction toward the belt 10 side. A receiving concave portion 43 capable of receiving the belt 10 is formed by the two walls 41a and 41b and the electrode 216b.

When the device main body 2 and the electrode 216b are installed on the fixing band 4 based on such a configuration, the belt 10 is received in the receiving concave portion 43 of the electrode 216b. Then, displacement of the electrode 216b in the width direction with respect to the belt 10 is regulated by the walls 41a and 41b of the receiving concave portion 43. For this reason, displacement of the relative positions of the belt 10 and the electrode 216b is prevented from occurring. That is, the receiving concave portion 43 constitutes a displacement regulation portion that regulates displacement of the relative positions of the belt 10 and the heartbeat detection portion 310.

Meanwhile, two walls 41a and 41b are exposed on both sides of the belts 9 and 10 in the short-side direction, in a state where the device main body 2 and the electrodes 216a and 216b are installed on the fixing band 4. For this reason, in order to prevent a pair of electrodes 216a and 216b from being short-circuited through clothes or the like, it is preferable to perform an insulation process such as application of an insulating coating to the walls 41a and 41b. Herein, an insulation processing method is not limited to insulating coating.

Therefore, according to the first modified example of the second embodiment, in addition to the same effects as those of the first embodiment and the second embodiment, the electrodes 216a and 216b can be caused to reliably adhere tightly to the chest of the user U, and thus it is possible to improve measurement accuracy of the heartbeat measurement device 211. In addition, displacement between the belts 9 and 10 and the heartbeat detection portion 310 can be prevented from occurring, and thus it is possible to reliably prevent the electrodes 216a and 216b of the heartbeat detection portion 310 from being short-circuited through clothes or the like due to exposure of the heartbeat detection portion 310 from the belt.

(Second Modified Example of Second Embodiment)

Figure 10:
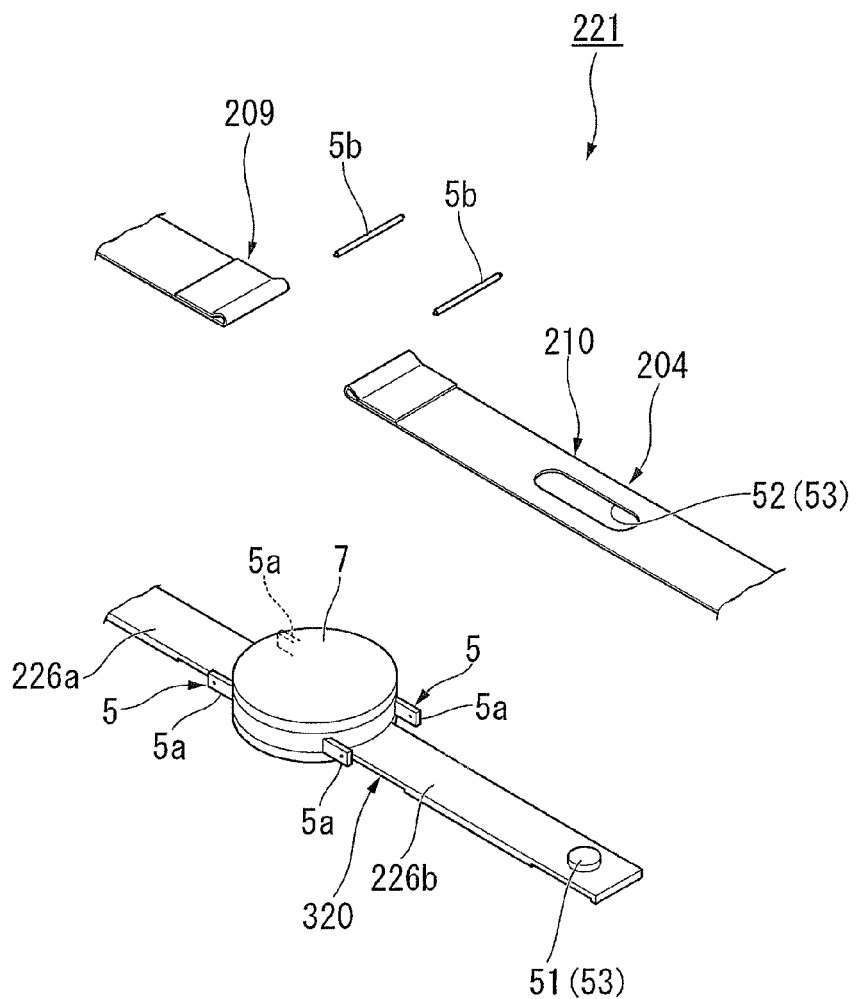
FIG. 10 is a perspective view illustrating the periphery of an electrode according to a second modified example of the second embodiment.

FIG. 10 is a perspective view illustrating the periphery of electrodes 226a and 226b according to a second modified example of the second embodiment.

Figure 11:
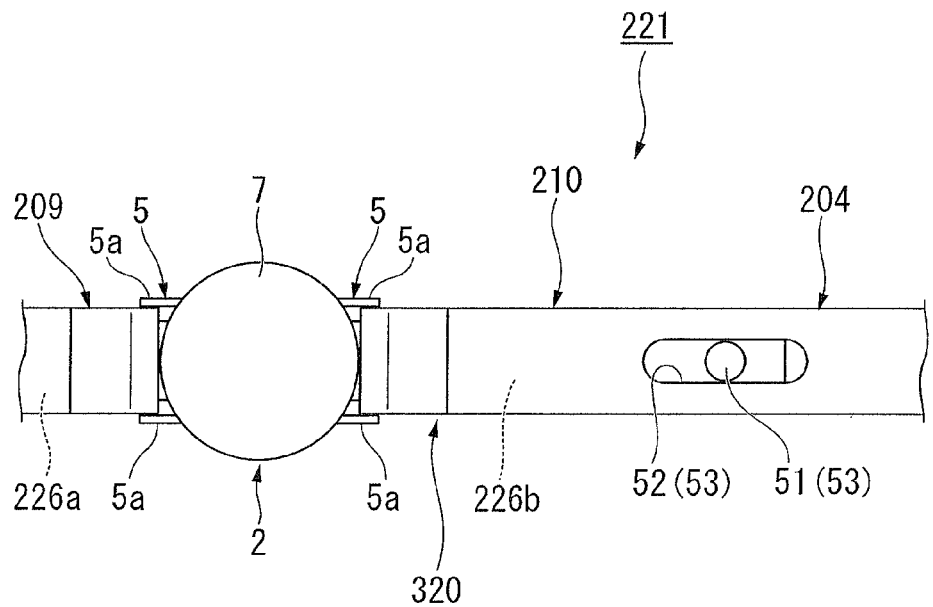
FIG. 11 is a top view illustrating the periphery of the electrode according to the second modified example of the second embodiment.

FIG. 11 is a top view illustrating the periphery of the electrodes 226a and 226b according to the second modified example of the second embodiment.

Subsequently, a heartbeat measurement device 221 according to the second modified example of the second embodiment will be described with reference to FIGS. 10 and 11.

In the heartbeat measurement device 201 according to the second embodiment, a pair of belts 9 and 10 are disposed so as to cover the electrodes 6a and 6b of the heartbeat detection portion 3 from the outside. On the other hand, the heartbeat measurement device 221 according to the second modified example of the second embodiment is different from that in the above-mentioned embodiment, in that a pair of belts 209 and 210 are disposed so as to cover the electrodes 226a and 226b of a heartbeat detection portion 320 from the outside, and a displacement prevention portion 53 is further formed in a pair of belts 209 and 210 and the electrodes 226a and 226b. Meanwhile, detailed description of the same configuration as that of the second embodiment will be omitted.

In addition, similarly to the first modified example of the second embodiment, hereinafter, description of the displacement prevention portion 53 on the belt 210 side will be made, while description the displacement prevention portion 53 on the belt 209 side will be omitted.

(Displacement Prevention Portion)

In the electrode 226b, a convex portion 51 protrudes toward the belt 210 side, at the end on the opposite side (right side in FIGS. 8 and 9) to the device main body 2. On the other hand, in the belt 210, a long hole portion 52 capable of inserting the convex portion 51 is formed at a place corresponding to the convex portion 51. The long hole portion 52 is formed in an elliptical shape along the long-side direction of the belt 210.

When the device main body 2 and the electrode 226b are installed on the belt 210 based on such a configuration, the convex portion 51 of the electrode 226b is inserted into the long hole portion 52 of the belt 210. Thereby, displacement of the electrode 226b in the width direction with respect to the belt 210 is regulated, that is, displacement of the relative positions of the belt 210 and the electrode 226b is prevented from occurring. That is, the displacement prevention portion constitutes a displacement regulation portion that regulates displacement of the relative positions of the belt 210 and the heartbeat detection portion 320.

Therefore, according to the second modified example of the second embodiment, it is possible to accomplish the same effect as that of the first modified example of the second embodiment.

Meanwhile, the convex portion 51 of the electrodes 226a and 226b is exposed to the outside through the long hole portion 52 of the belts 209 and 210, in a state where the device main body 2 and the electrodes 226a and 226b are installed on the fixing band 204. For this reason, in order to prevent a pair of electrodes 226a and 226b from being short-circuited through clothes or the like, it is preferable to perform an insulation process such as application of an insulating coating to the convex portion 51. Herein, an insulation processing method is not limited to insulating coating. For example, the convex portion 51 may be formed by a separate member from the electrodes 226a and 226b, that is, an insulating member, and may be installed on the electrodes 226a and 226b. In addition, the electrodes 226a and 226b and the convex portion 51 can also be formed by two-color molding.

The present invention is not limited to the above-mentioned embodiments, and various changes may be added to the above-mentioned embodiments without departing from the scope of the present invention.

In the first embodiment, the engagement portion between the elastic strap 8 (fixing band 4) and the device main body 2 is constituted by the hook portion 12b of the strap attaching and detaching member 12 and the engaged portion 5b of the connection member 5. In addition, in the second embodiment, the engagement portion between the belts 9 and 10 (fixing band 4) and the device main body 2 is constituted by the hook-and-loop fastener 33 provided to the belt bodies 9c and 10c and the belt ends 9a and 10a.

However, the engagement portion provided between the fixing band 4 and the device main body 2 is not limited to the above-mentioned embodiment.

Figure 12:
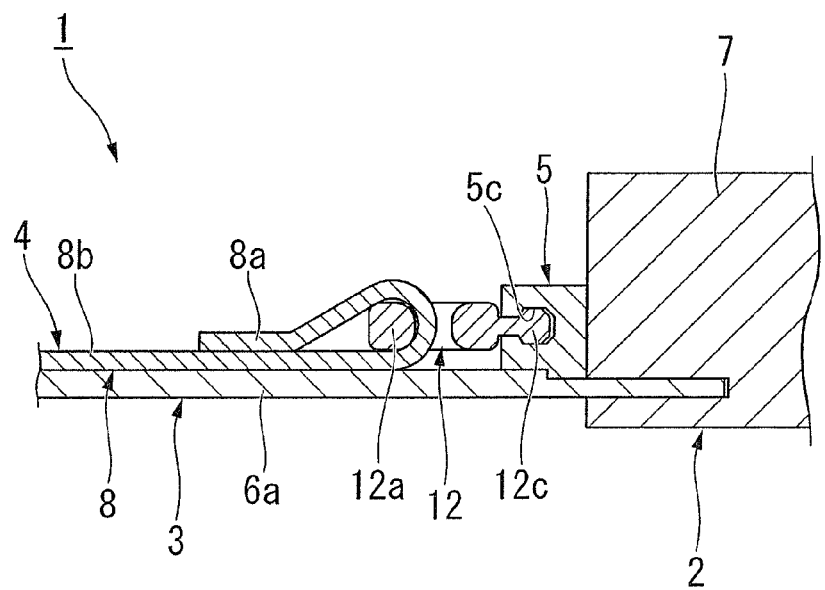
FIG. 12 is an explanatory diagram illustrating another engagement portion.

FIG. 12 is an explanatory diagram illustrating another engagement portion.

As shown in FIG. 12, a dovetail groove-shaped slot 5c is formed along the width direction (paper front-and-back direction in FIG. 12) of the fixing band 4, in the connection member 5 of the device main body 2. In addition, a rail 12c corresponding to the shape of the slot 5c is formed in the strap attaching and detaching member 12. The rail 12c is inserted into and extracted from the dovetail groove-shaped slot 5c from the width direction of the fixing band 4, so that the fixing band 4 and the device main body 2 are detachably installed. In this manner, the engagement portion between the fixing band 4 and the device main body 2 may be constituted by the slot 5c formed in the connection member 5 of the device main body 2 and the rail 12c formed in the strap attaching and detaching member 12.

In this manner, the engagement portion between the fixing bands 4 and 204 and the device main body 2 is not limited to the above-mentioned embodiment, but various engagement portions can be adopted.

In the above-mentioned first modified example of the second embodiment, the electrodes 216a and 216b are provided with the guide portion 41. The guide portion 41 may be applied to the first embodiment. Thereby, it is possible to regulate displacement of the elastic strap 8.

In addition, in the first modified example of the above-mentioned second embodiment, the displacement regulation portion that prevents displacement of the relative positions of the belts 9 and 10 and the electrodes 216a and 216b by providing the electrodes 216a and 216b with the guide portion 41 has been described. In the second modified example of the above-mentioned second embodiment, the displacement regulation portion that prevents displacement of the relative positions of the belts 209 and 210 and the electrodes 226a and 226b from occurring by protrusively forming the convex portion 51 in the electrodes 226a and 226b and forming the long hole portion 52, capable of inserting the convex portion 51, in the belts 209 and 210 has been described. However, the displacement regulation portion is not limited thereto, but may be a structure capable of preventing displacement of the relative positions of the belts 9 and 10 and the electrodes 216a and 216b, or displacement of the relative positions of the belts 209 and 210 and the electrodes 226a and 226b.

For example, displacement of each relative position may be prevented from occurring by providing a hook-and-loop fastener to the belts 9 and 10 and the electrodes 6a and 6b in the second embodiment.

In addition, in each embodiment and each modified example mentioned above, a case has been described in which the device main body 2 and the heartbeat detection portions 3, 310, and 320 are integrally formed in the heartbeat measurement devices 1, 201, 211, and 221 that measure the heart rate of the user U as a biological information detection device, and the device main body 2 and the heartbeat detection portion 3 are installed on the chest of the user U using the fixing bands 4 and 204. However, such a configuration is not only applied to the heartbeat measurement devices 1, 201, 211, and 221, but is also capable of being applied to various biological information detection devices. For example, as a biological information detection device, the configurations of the above-mentioned embodiments can be applied to devices that measure blood pressure, body temperature, myogenic potential and the like.

In each embodiment and each modified example mentioned above, a material having elasticity is adopted for the elastic strap 8, and a non-elastic material is adopted for the belts 9, 10, 209, and 210. However, a material having a moisture retaining property may be further adopted for the elastic strap 8 and the belts 9, 10, 209, and 210. Specifically, a material containing polyester, nylon or the like as a main ingredient may be adopted for the elastic strap 8 and the belts 9, 10, 209, and 210. In addition, a moisture absorbing material such as PVA sponge may be provided to the inner surface side of the elastic strap 8 or the belts 9, 10, 209, and 210. Thereby, it is possible to moisturize the periphery of the heartbeat detection portions 3, 310, and 320, and to improve detection performance of the heartbeat measurement devices 1, 201, 211, and 221.

What is claimed is:

1. A biological information detection device comprising:
a device main body;
a biological signal detection portion formed integrally with the device main body, the biological signal detection portion having electrodes configured to be brought into contact with a biological surface of a human body;
a fixing portion formed in a belt shape for fixing the device main body and the biological signal detection portion to the human body; and
an engagement portion for detachably mounting the device main body to the fixing portion, the engagement portion comprising first connecting members protruding from respective opposite sides of the device main body at positions corresponding to the electrodes and second connecting members extending from respective end portions of the fixing portion for detachable engagement with the respective first connecting members,
wherein the fixing portion includes at least an elastic strap and a non-elastic belt connected to at least one end of the elastic strap in a long-side direction of the fixing portion; and wherein the non-elastic belt is configured to cover the biological signal detection portion and to be detachably mounted on the device main body through the engagement portion.

2. The biological information detection device according to claim 1, further comprising a displacement regulation portion provided between the belt and the biological signal detection portion for regulating a relative positional displacement therebetween.

3. A biological information detection device comprising:
a device main body;
a biological signal detection portion formed integrally with the device main body, the biological signal detection portion having electrodes configured to be brought into contact with a biological surface of a human body;

a fixing portion formed in a belt shape for fixing the device main body and the biological signal detection portion to the human body; and an engagement portion for detachably mounting the device main body to the fixing portion, the engagement portion comprising first connecting members protruding from respective opposite sides of the device main body at positions corresponding to the electrodes and second connecting members extending from respective end portions of the fixing portion for detachable engagement with the respective first connecting members, wherein the fixing portion comprises an elastic strap and a non-elastic belt interconnected between the elastic strap and the device main body via the engagement portion.

4. The biological information detection device according to claim 3, wherein the first connecting members comprise two pairs of arms extending from respective opposite sides of the device main body; and wherein the second connecting members are provided at respective end portions of the non-elastic belt for detachable engagement with the respective pairs of arms.

5. The biological information detection device according to claim 3, wherein the electrodes comprise a pair of electrodes extending from the respective opposite sides of the device main body; and wherein the first connecting members comprise two pairs of arms extending from the respective opposite sides of the device main body, one of the pair of arms extending along respective opposite sides of one of the pair of electrodes and the other of the pair of arms extending along respective opposite sides of the other of the pair of electrodes.

6. The biological information detection device according to claim 5, wherein the non-elastic belt comprises a pair of non-elastic belt sections disposed so as to cover the respective electrodes.

7. The biological information detection device according to claim 3, wherein the electrodes are not directly connected to the fixing portion.

8. The biological information detection device according to claim 3, further comprising a displacement regulation portion for regulating displacement of relative positions between the non-elastic belt and the biological signal detection portion.

9. The biological information detection device according to claim 8, wherein the non-elastic belt comprises non-elastic belt sections; and wherein the displacement regulation portion comprises convex portions provided on respective ones of the electrodes and the non-elastic belt sections and hole portions formed on respective ones of the other of the electrodes and the non-elastic belt sections.

10. A biological information detection device comprising:
a main body portion having two pairs of first connecting members protruding from respective opposite sides thereof;

a biological signal detection portion having a pair of electrodes that extend from the respective opposite sides of the main body portion along respective directions of extension of the first connecting members, the pair of electrodes being configured to be brought into contact with a biological surface of a human body to detect a biological signal of the human body; and a mounting portion for removably mounting the main body portion and the detection portion to the human body, the mounting portion having second connecting members disposed at respective end portions thereof for detachable engagement with the respective first connecting members of the biological signal detection portion, wherein the mounting portion comprises an elastic strap and a non-elastic belt interconnected between the elastic strap and the main body portion via the first and second connecting members.

11. The biological information detection device according to claim 10, wherein the first connecting members comprise two pairs of arms extending from respective opposite sides of the main body portion; and wherein the second connecting members are provided at respective end portions of the non-elastic belt for detachable engagement with the respective pairs of arms.

12. The biological information detection device according to claim 10, further comprising a displacement regulation portion for regulating displacement of relative positions between the non-elastic belt and the biological signal detection portion.

* * * * *